United States Patent
Kim et al.

(10) Patent No.: US 6,737,401 B2
(45) Date of Patent: May 18, 2004

(54) METHODS OF EVALUATING PROTEIN FORMULATION STABILITY AND SURFACTANT-STABILIZED INSULIN FORMULATIONS DERIVED THEREFROM

(75) Inventors: Seonyoung Kim, Winnetka, CA (US); William P. Van Antwerp, Valencia, CA (US); Todd M. Gross, Saugus, CA (US); Poonam S. Gulati, La Canada, CA (US)

(73) Assignee: Metronic MiniMed, Inc., Northridge, CA (US)

( * ) Notice: Subject to any disclaimer, the term of this patent is extended or adjusted under 35 U.S.C. 154(b) by 52 days.

(21) Appl. No.: 09/981,968

(22) Filed: Oct. 18, 2001

(65) Prior Publication Data

US 2003/0054979 A1 Mar. 20, 2003

Related U.S. Application Data

(60) Provisional application No. 60/302,345, filed on Jun. 28, 2001.

(51) Int. Cl.[7] ............................................. A61K 38/28
(52) U.S. Cl. ............................. 514/4; 514/2; 530/300; 530/303; 435/7.1; 435/4
(58) Field of Search ................... 514/2, 3, 4; 530/300, 530/303, 350

(56) References Cited

U.S. PATENT DOCUMENTS

| | | | |
|---|---|---|---|
| 4,439,181 A | 3/1984 | Blackshear et al. | |
| 4,652,548 A | 3/1987 | Chance et al. | |
| 4,839,341 A | 6/1989 | Massey et al. | |
| 4,885,164 A | 12/1989 | Thurow | |
| 4,988,675 A | 1/1991 | Froesch et al. | |
| 5,149,777 A | 9/1992 | Hansen et al. | |
| 5,474,978 A | 12/1995 | Bakaysa et al. | |
| 5,514,646 A | 5/1996 | Chance et al. | |
| 5,527,307 A | 6/1996 | Srisathapat et al. | |
| 5,569,186 A | 10/1996 | Lord et al. | |
| 5,637,095 A | 6/1997 | Nason et al. | |
| 5,641,744 A | 6/1997 | Cooper | |
| 5,753,681 A | 5/1998 | Fujiwara et al. | |
| 5,783,556 A | 7/1998 | Clark et al. | |
| 5,952,297 A | 9/1999 | De Felippis et al. | |
| 5,958,909 A | 9/1999 | Habener | |
| 6,034,054 A | 3/2000 | DeFelippis et al. | |
| 6,133,229 A | 10/2000 | Gibson et al. | |
| 6,136,784 A | 10/2000 | L'Italien et al. | |
| 6,153,632 A | 11/2000 | Rieveley | |
| 6,166,042 A | 12/2000 | Ikeda et al. | |
| 6,166,043 A | 12/2000 | Ikeda et al. | |
| 6,169,099 B1 | 1/2001 | Ikeda et al. | |
| 6,169,100 B1 | 1/2001 | Ikeda et al. | |
| 6,174,856 B1 | 1/2001 | Langballe et al. | |
| 6,211,144 B1 | 4/2001 | Havelund | |
| 6,268,343 B1 | 7/2001 | Knudsen et al. | |
| 6,323,311 B1 | 11/2001 | Liu et al. | |
| 2001/0031726 A1 | 10/2001 | Van Antwerp et al. | |

FOREIGN PATENT DOCUMENTS

| | | |
|---|---|---|
| EP | 0 726 075 A1 | 8/1996 |
| EP | 0 925 792 A2 | 6/1999 |
| EP | 1 090 640 A2 | 4/2001 |
| WO | WO 92/20366 | 11/1992 |
| WO | WO 96/02270 | 2/1996 |
| WO | WO 98/56406 | 12/1998 |
| WO | WO 98/57636 | 12/1998 |
| WO | WO 99/43705 | 9/1999 |
| WO | WO 99/64589 | 12/1999 |

OTHER PUBLICATIONS

Nielsen et al. "Effect of environmental factors on the kinetics of insulin fibril formation: elucidation of the molecular mechanism" 2001, Biochemistry, vol. 40, pp–6036–6046.*

Sluzky et al. " Kenitics of insulin aggrgation in aqueous solutions upon agitation in the presence of hydrophobic surfaces"1991, Proc. Natl. Acad. Sci. USA, vol. 88, pp–9377–9381.*

Ahren et al., "Effects of Glucagon–Like Peptide–1 on Islet Function and Insulin Sensitivity in Noninsulin–Dependent Diabetes Mellitus," J. of Clin. Endocrinology and Metabolism, 1997, 82(2):473–478.

Brange et al., "Chemical Stability of Insulin: 3. Influence of Excipients, Formulation, and pH," Acta Pharmaceutica Nordica, 1992, 4(3): 149–158.

Gutniak et al., "Antidiabetogenic Effect of Glucagon–Like Peptide–1 (7–36) Amide in Normal Subjects and Patients with Diabetes Mellitus," The New England Journal of Medicine, 1992, 1316–1322.

Holst, "GLP–1 in NIDDM," Diabetic Med., 1996, (9 suppl. 6), pp. S156–160.

Jones et al., "Surfactant–Stabilized Protein Formulations," Therapeutic Protein and Peptide Formulations and Delivery, 1997, American Chemical Society Publication, chapter 12, p. 206.

(List continued on next page.)

Primary Examiner—Christopher Tate
Assistant Examiner—Roy Teller
(74) Attorney, Agent, or Firm—Gates & Cooper LLP

(57) ABSTRACT

Embodiments of the invention are directed to a method of estimating the physical stability of a protein formulation. A particular embodiment of the invention places the protein formulation under an agitational stress that causes the protein to aggregate at an accelerated rate. In one embodiment, the change in protein aggregation is monitored spectroscopically using Thioflavin-T. Embodiments of the invention then utilize a survival curve analysis to ascertain the relative physical stability of the different protein formulations under study. This method was used to develop novel surfactant-stabilized insulin formulations in a rapid, cost efficient manner, thus illustrating the utility of the inventive method to the discovery and development of pharmaceutical protein formulations.

7 Claims, 9 Drawing Sheets

OTHER PUBLICATIONS

LeVine, III, "Thioflavine T Interaction with Synthetic Alzheimer's Disease β–amyloid Peptides: Detection of Amyloid Aggregation in Solution," Protein Science, 1993, 2: 404–410.

Mokuda et al., "Plasma Glucose Response After Intravenous Injection of Tolbutamide in Insulin–Treated Type I and Type II Diabetic Patients," Exp. Clin. Endocrinol., 1988, 91(3): 265–270.

Nielsen et al., "Effect of Environmental Factors on the Kinetics of Insulin Fibril Formation: Elucidation of the Molecular Mechanism," Biochemistry, 2001, 40: 6036–6046.

Quinn et al., "Minimizing the Aggregation of Neutral Insulin Solutions," Jnl. Of Pharmaceutical Sciences, 1983, 72(12): 1472–1473.

Ryan et al., "Inslunotropic Hormone Glucagon–Like Peptide–1–(7–37) Appears not to Augment Insulin–Mediated Glucose Uptake in Young Men During Euglycemia," J. of Clin. Endocrinology and Metabolism, 1998, 83(7): 2399–2404.

Sluzky et al., "Kinetics of Insulin Aggregation in Aqueous Solutions Upon Agitation in the Presence of Hydrophobic Surfaces," Proc. Of Natl. Acad. Sciences, 1991, 88:9377–9381.

Toft–Nielsen et al., "The Effect of Glucagon–Like Peptide I (GLP–I) on Glucose Elimination in Healthy Subjects Depends on the Pancreatic Glucoregulatory Hormones," Diabetes, 1996, 45: 552–556.

* cited by examiner-

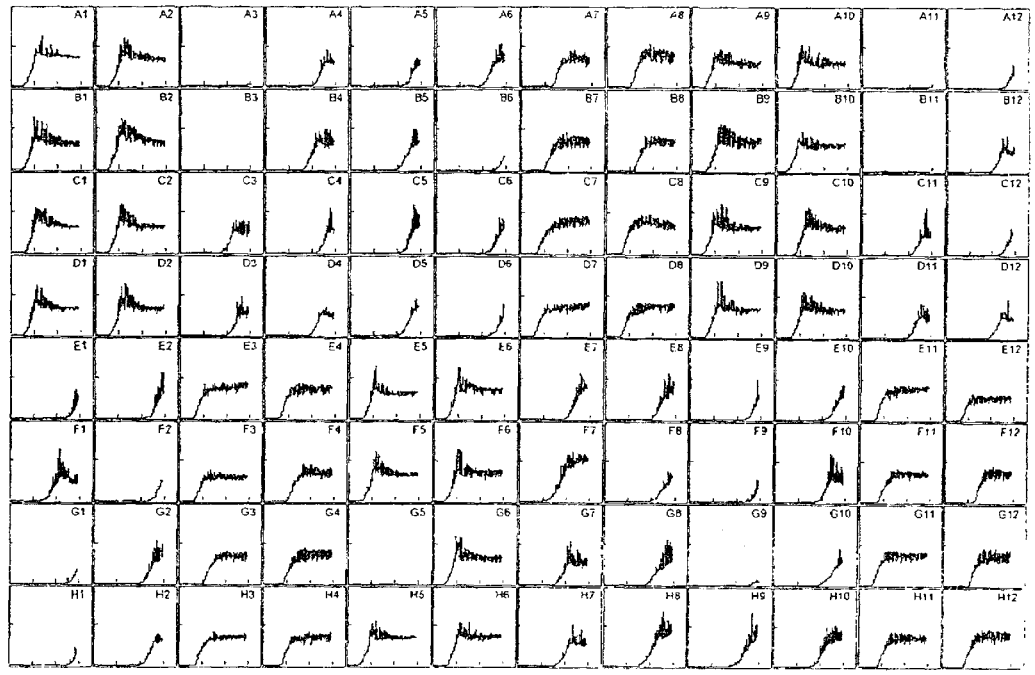

Fluoroskan Val 15 SEF---end of run (122 hr) (Y max = 1000)

This snap shot gives you a quick look at what is going on without any further analysis You can tell that some samples fully aggregated, some partially aggregated and some did not aggregate at all This snap shot picture is taken at every measurement during the entire run and therefore you can evaluate which formulation is more stable before run is over and we analyze the data.

Figure 1

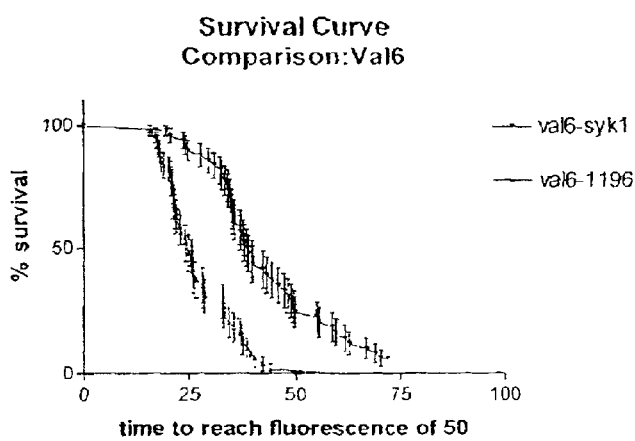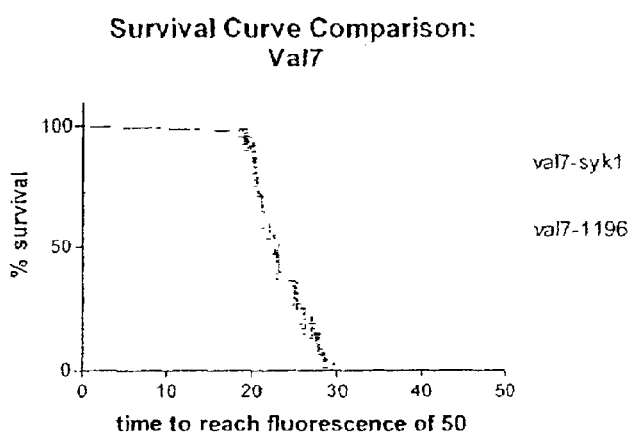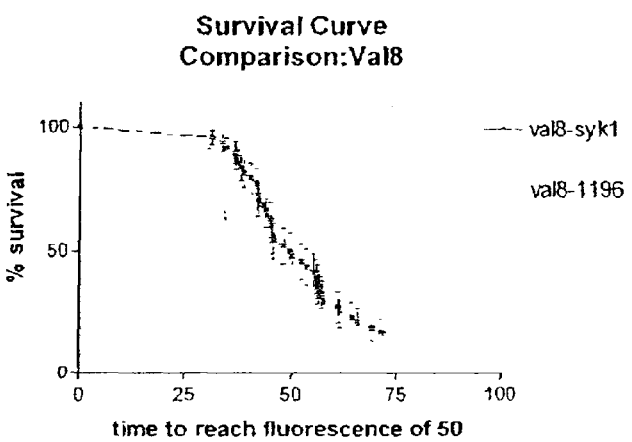
Figure 3

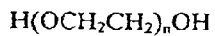
Polyethylene glycol
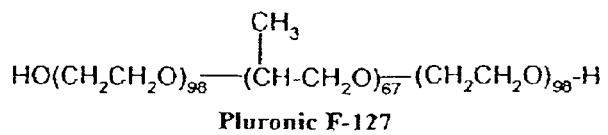
Pluronic F-127
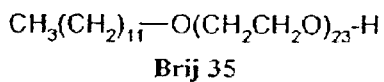
Brij 35
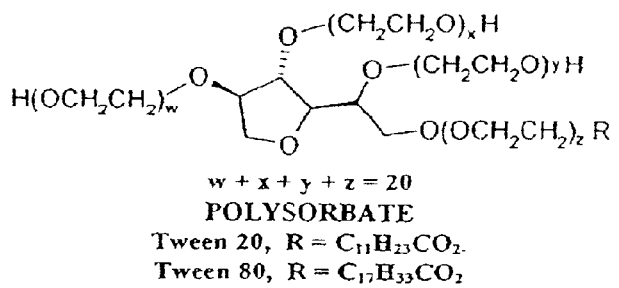
$w + x + y + z = 20$
POLYSORBATE
Tween 20, $R = C_{11}H_{23}CO_2$
Tween 80, $R = C_{17}H_{33}CO_2$
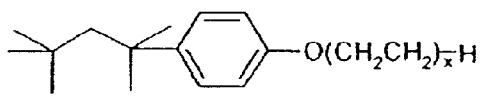
Polyethylene glycol ether
Triton X-100, x = 9 - 10 (average)
Triton X-114, x = 7 - 8 (average)
Chemical structures of nonionic surfactants of pharmaceutical interest
Figure 5

US 6,737,401 B2

METHODS OF EVALUATING PROTEIN FORMULATION STABILITY AND SURFACTANT-STABILIZED INSULIN FORMULATIONS DERIVED THEREFROM

This application claims the benefit of Provisional Application No. 60/302,345 filed Jun. 28, 2001

FIELD OF THE INVENTION

Embodiments of the invention are directed to accelerated methods of determining the relative physical stability of a protein formulation and surfactant-stabilized insulin formulations.

BACKGROUND OF THE INVENTION

The physical stability of pharmaceutical protein formulations is of paramount importance since there is always a time delay between production of the protein formulation and its delivery to an appropriate patient. The physical stability of a protein formulation becomes even more critical when using drug delivery devices to dispense the protein formulation, such as infusion pumps and the like. When these delivery devices are used, the protein formulation is generally stored in the device, which is either worn close to the body or implanted within the body. In either case, a patient's own body heat and body motion, plus turbulence produced in the delivery tubing and pump, impart a high amount of thermo-mechanical energy to a protein formulation. Thus, the use of such infusion delivery devices places a high degree of thermo-mechanical stress on the protein formulation to be delivered. Additionally, infusion delivery devices expose the protein to hydrophobic interfaces that are found in the delivery syringes and catheters. These interfacial interactions tend to destabilize the protein formulation by inducing denaturation of the native structure of the protein at these hydrophobic interfaces.

Analytical tools for assessing the physical stability of protein formulations, in particular insulin formulations, have been developed. These analytical methods, however, generally require long test runs of 20 or more days, as well manual intervention during the test period. Moreover, most protein formulations contain numerous excipients that are added to the formulation to further stabilize the protein. For example, a typical insulin formulation may contain five or more excipients, such as a particular buffer system, isotonic substances, metal ions, preservatives and one or more surfactants.

Given the long test runs and manual intervention required to assess the physical stability of a new insulin formulation, as well as the need to vary five or more excipients over a particular concentration range during the analytical process, the development of new formulations is costly in terms of time and resources. Moreover, even for the evaluation of new batches of a known protein formulation, such as in quality control analysis, current state of the art methods are less than desirable.

Since the requirements of current protein formulation evaluation methods are not conducive to the rapid development of novel and more physically stable protein formulations, a reliable, time- and resource-efficient analytical method is desired. Such an analytical tool would enable the rapid development of novel protein formulations, as well as the rapid identification of protein formulation stability in quality control procedures.

SUMMARY OF THE DISCLOSURE

Embodiments of the invention are directed to methods of evaluating the physical stability of a protein formulation. These methods includes two phases. The first phase includes the following steps. Preparing a statistically relevant number of identical samples of a protein formulation to yield a one or more sample types, where the protein is susceptible to changes in its native conformation yielding non-native conformers of the protein. A small molecular agent or probe that yields a change upon binding to a non-native conformer of the protein is then added to the samples. A controlled stress is then applied to all sample types, where the controlled stress applied causes the protein to exhibit a change in its native conformation. The sample types are then monitored to yield time-dependent data that are related to a degree of protein conformational change for each sample type. The second phase includes applying a survival analysis to the data obtained for each sample type and comparing the survival analysis for each sample type to determine the relative physical stability of the protein formulations under evaluation.

A preferred controlled stress suitable for use in embodiments of the invention is agitation. A preferred method to monitor the change in protein conformation is via fluorescence. An example of a protein conformational change suitable for use in the invention is the change in the physical structure of insulin from its native conformation to the fibril form of insulin.

From the use of a particular embodiment of the invention, novel surfactant-stabilized insulin formulations were developed. These novel insulin formulations include a buffer system, an isotonicity agent, a preservative, metal ions, and a non-ionic surfactant selected from at least a polysorbate, a poloxyethylene ether, a polyethylene glycol ether, and mixtures of these surfactants. The preferred insulin for use in these novel formulations is human insulin, preferably a human recombinant of insulin. The preferred insulin concentrations for use in the formulations of the invention is about 2 U/ml to about 1000 U/ml, most preferably about 400 U/ml.

An unexpected property of the novel surfactant stabilized insulin formulations of embodiments of the invention is that these formulations provide a greater stabilization to insulin than the prior art, Genapol stabilized formulations. Moreover, the surfactants suitable for use in formulations of the invention are FDA regulatory approved surfactants, thus further demonstrating the use of these novel formulations in pharmaceutical preparations of insulin.

These highly stable, surfactant-stabilized insulin formulations are particularly well-suited for use in infusion devices for the delivery of insulin to a patient. Thus, another aspect of the invention is directed to insulin infusion devices, which include an insulin pump system and a surfactant-stabilized insulin formulation including insulin and a non-ionic surfactant selected from at least a polysorbate, a poloxyethylene ether, a polyethylene glycol ether, and mixtures of these surfactants.

BRIEF DESCRIPTION OF THE DRAWINGS

A detailed description of embodiments of the invention will be made with reference to the accompanying drawings, wherein like numerals designate corresponding parts in the several figures.

FIG. 1 shows a snap shot of the aggregation behavior for particular insulin formulations in a 96-well microplate.

FIG. 3 is a graphic representation of a survival curve comparison of three experimental runs used to validate embodiments of the present invention.

FIG. 5 is a representation of the chemical structure of some FDA regulatory approved surfactants.

DETAILED DESCRIPTION OF THE PREFERRED EMBODIMENTS

I. Definitions

Figure 2:
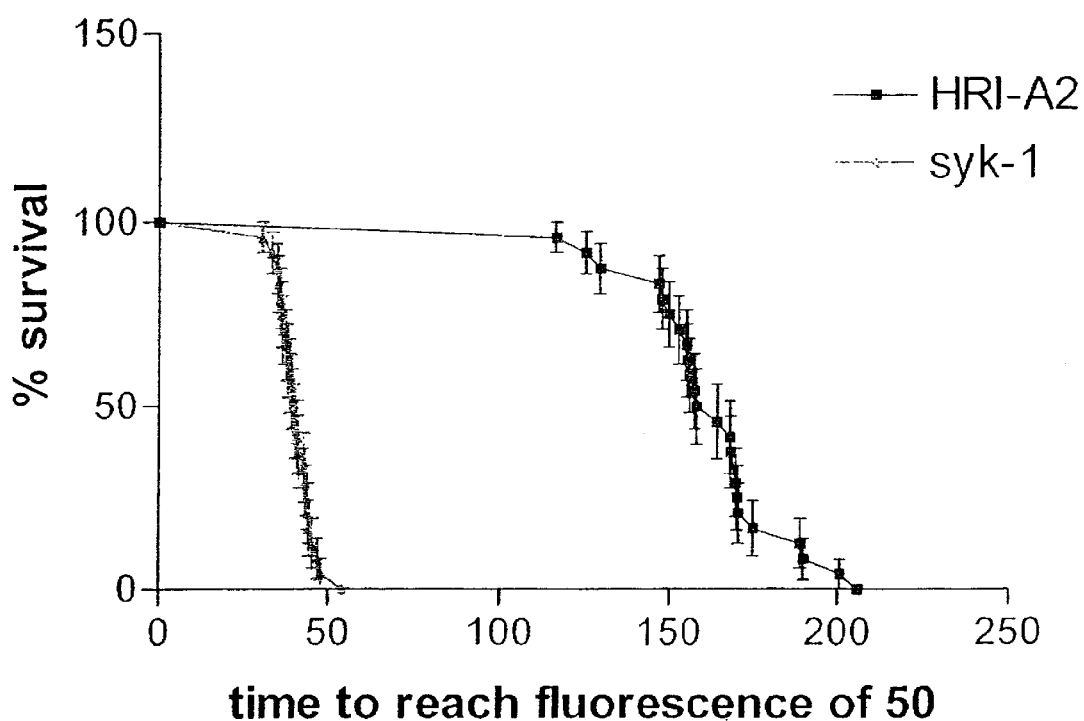
FIG. 2 is a graphic representation of the survival curve analysis data shown in Table 2.

Unless otherwise specified, the term "insulin" as used herein is intended to refer to any insulin, including but not limited to human and animal insulins, recombinant insulins, semi-synthetic insulins, insulin analogues where one or more amino acid residues of the protein sequence of human insulin have been deleted or replaced by other amino acid residues or additional amino acid residues not found in human insulin have been added, and derivatives of human insulins or analogues where at least one organic substituent is bound to one or more of the amino acid residues, or the like.

The term "aqueous" as used herein refers to a water-based protein formulation, but may optionally contain additional solvents, e.g., a small amount of a water-miscible solvent.

Generally, the phrase "physical stability of a protein formulation," as used herein, refers to the ability of a particular protein formulation to maintain the native, active structure of a protein as the protein is exposed to thermo-mechanical stresses over time. More particularly, the term "physically stability of a protein formulation" generally refers to the tendency of a protein formulation to undergo conformational changes over time yielding non-native conformers of the protein that deviate from the native conformation of the protein, i.e., to denature, including partial denaturation, regardless of whether the non-native conformer of the protein forms higher molecular weight aggregates or precipitates. In terms of insulin formulations and other protein formulations where higher molecular weight, insoluble aggregates result in decreased activity of the protein formulation, the term "physical stability" refers to the tendency of a protein formulation to form biologically inactive and/or insoluble aggregates of the protein as a result of exposure of the protein to thermo-mechanical stresses, as well as the tendency of a protein formulation to form biologically inactive and/or insoluble aggregates of the protein as a result of interaction with interfaces and surfaces that are destabilizing, such as hydrophobic surfaces and interfaces. The interaction of a protein with hydrophobic surfaces and interfaces is also referred to as interfacial denaturation or interfacial tension. In the case of insulin, these biologically inactive and/or insoluble aggregates are generally polymeric fibril forms of insulin. A related parameter to the "physical stability of a protein formulation" is its solubility in that higher molecular weight aggregates and denatured forms of a protein, including partially denatured forms of a protein, which are generally less soluble than their non-aggregated, lower molecular weight counterparts and native forms of the protein. Another related parameter to the "physical stability of a protein formulation" is the protein concentration in that physically stable formulations become less physically stable as the concentration of the protein is increased or decreased.

The various forms of the verb "to aggregate" refer to a process where individual protein molecules or complexes formed from individual protein molecules associate with one another. Some aggregates have biological activity while other forms of aggregates do not. An exemplary biologically active protein aggregate is a polymeric assembly comprising insulin monomers to form an insulin hexamer. In the case of insulin, however, both the monomer and the hexamer have biological activity in the body. Insulin can also form other forms of biologically inactive protein aggregates which generally include polymeric fibrils. These fibrils are inactive aggregates of insulin that exist largely in a beta sheet conformation rather than in the native conformation of insulin, which is largely alpha helical.

The term "interfacial denaturation" or "interfacial tension" as used herein refers to a process of protein denaturation that results from exposure of the protein to hydrophobic surfaces, e.g., air-water interfaces and hydrophobic polymer-water interfaces, e.g., where the hydrophobic polymer is a Teflon material, silicone material, saran material, plastic materials, or the like.

The term "physical stress" as used herein refers to any thermo-mechanical stress that is placed on a protein formulation, such as agitational, vibrational stresses, and the like.

In embodiments of the present invention, a "unit" ("U") approximately corresponds to 6.2 to 6.9 nmol of insulin.

The term "Tris" as used herein refers to 2-amino-2-hydroxymethyl-1,3-propanediol and to any pharmacologically acceptable salt thereof. The free base and the hydrochloride forms are two common types of Tris. Tris is also known as tremethylol aminomethane, tromethamine and tris(hydroxylmethyl)aminomethane.

The term "phenolic preservative" as used herein generally refers to art accepted phenolic preservatives, such as chlorocresol, m-cresol, phenol and mixtures of these preservatives, or the like.

An "isontonicity agent" is a chemical substance that is physiologically tolerated and imparts a suitable tonicity to a formulation which prevents the net flow of water across cell membranes that are in contact with the formulation. Chemical substances such as glycerin are commonly used for such purposes at suitable concentrations. Other possible isotonicity agents includes salts, e.g. sodium chloride, glucose, dextrose and lactose, or the like.

II. Methods of Evaluating the Physical Stability of Protein Formulations: The Accelerated Physical Stability Method Embodiments of the present invention are directed to reliable, time- and cost-efficient methods of evaluating the relative physical stability of a particular protein formulation. Thus, embodiments of the invention are useful analytical tools for developing new protein formulations with increased physical stability, as well as for use in evaluating the physical stability of newly prepared batches of known protein formulations in quality control procedures, or the like.

Embodiments of the present invention encompass a fully automated assay of protein formulation stability that generally requires less than 7 days to evaluate even the most physically stable protein formulations. Embodiments of the inventive method generally require two main steps. First, statistically relevant experimental data reflective of the physical stability of particular protein formulations is gathered. In a second step, these data are analyzed using a statistical method utilizing survival curve analyses. The utility of the accelerated physical stability methods of the invention is further demonstrated by the development of novel surfactant-stabilized insulin formulations using an embodiment of the invention. These novel protein formulations are disclosed in Section III below.

i) Probing the Physical Status of a Protein Formulation: The First Step of the Accelerated Physical Stability Method Embodiments of the inventive method involve placing a small amount of a protein formulation to be evaluated under a controlled stress. The preferred sample volume is about 50 $\mu$l to about 500 $\mu$l, most preferably about 200 $\mu$l. However, other sample volumes can be used. Embodiments of the invention can accommodate sample volumes from 1 $\mu$l to 1 ml. The medium chosen for the analysis can be any medium in which the physical stability of a particular protein is desired to be evaluated, such as aqueous solutions, organic solvents, and the like. Further, the medium chosen can be a liquid, an emulsion, a gel, or the like.

The controlled stress is externally applied to one or more protein formulations under evaluation. This controlled stress is physically translated to the protein contained in a particular formulation. Thus in embodiments of the invention, an application of stress yields an accelerated rate of change in the physical state of the protein formulations under evaluation. More specifically, the applied stress induces one or more non-native states of the protein, i.e. non-native conformational states, to be produced at an accelerated rate. These non-native states of the protein generally are not biologically active and represent a lower energy state of the protein. The time required for a certain amount of a particular protein to undergo a physical change to one or more of its non-native states is reflective of the physical stability of the protein formulation. Moreover, a relative comparison of two or more protein formulations that differ in composition yields the relative physical stability of the proteins formulations under evaluation.

In embodiments of the invention, this change in the physical state of a protein, i.e., production of one or more non-native protein states, is detected spectroscopically using an spectroscopic probe that preferentially binds to a non-native form of the protein, as compared to its binding to the native form of the protein. The detection of this induced change in protein state, caused by the applied stress, can be observed by following a concomitant change in spectra of the spectroscopic probe upon its binding to a non-native state of the protein. This change in the spectra of the spectroscopic probe can be monitored by numerous spectral techniques, such as fluorescence, absorbance, nuclear magnetic resonance (NMR), circular dichroism (CD), or the like.

Other embodiments of the invention include monitoring a change in the physical state of protein by observing changes in the bulk physical properties of the protein formulations under evaluation. These techniques involve monitoring a change in shape and/or size of the protein as a function of the applied stress, including monitoring changes in the frictional properties, viscosity, turbidity, light scattering, or the like, of the protein formulations under evaluation. The use of these techniques in embodiments of the invention do not require the addition of a spectroscopic agent to probe the change in the conformational state of the protein in a given formulation.

The stress applied is preferably a controlled physical stress, including agitational, vibrational, rotational, shearing, ultrasonic stresses, or the like. Other types of applied stress are included in embodiments of the invention, such as thermal stress, photochemical stress, or the like. When applying a thermal stress, concomitant changes in the physical states of the protein result, however, thermal stress also may affect the chemical state of the protein. In embodiments of the invention utilizing a photochemical stress, generally changes in the physiochemical state of the protein is probed. Further, the controlled stress applied can be a combination of two or more stresses, such as agitation of the protein formulations of interest at elevated temperatures.

For embodiments of the present invention that include a spectroscopic agent or probe of the conformational status of a protein, the probe is preferably a small molecule that preferentially binds to a non-native conformer of the protein. One example of a small molecular spectroscopic probe of protein structure is Thioflavin-T. Thioflavin-T is a fluorescent dye that has been widely used for the detection of amyloid fibrils. In the presence of fibrils, and perhaps other protein configurations as well, Thioflavin-T gives rise to a new excitation maximum at about 450 nm and enhanced emission at about 482 nm when bound to a fibril protein form. Unbound Thioflavin-T is essentially non-fluorescent at these wavelengths. Recently, Thioflavin-T has been used to elucidate the mechanism of fibril formation in insulin.[1]

[1]Nielson, L., Khurana, R., Coats, A., Frokjaer, S., Brange, J., Vyas, S., Uversky, V., and Fink, A. *Biochemistry*, 2001, 40, p.6036.

Other small molecules can be used as probes of the changes in protein structure from native to non-native states. Examples of other small molecular, spectroscopic probes is the "exposed hydrophobic patch" probe and the "exposed coordination site" probe. As is the case with Thioflavin-T, these small molecular, spectroscopic probes yield a spectroscopic change upon binding to a non-native form of the protein of interest, such as a change in fluorescence, a change in absorbance, a change in circular dichroism, and the like.

The "hydrophobic patch" probe preferentially bind to exposed hydrophobic patches of a protein. These hydrophobic patches are generally buried within the tertiary structure of a protein in its native state, but become exposed as a protein begins to unfold or denature. Examples of these small molecular, spectroscopic probes are aromatic, hydrophobic dyes, such as anthracene, acridine, phenanthroline, or the like. Other spectroscopic probes are metal-amino acid complexes, such as cobalt metal complexes of hydrophobic amino acids, such as phenylalanine, leucine, isoleucine, methionine, and valine, or the like.

Another example of a small molecular probe, is a probe of the coordination saturation in non-native states of a metalloprotein. Examples of these molecular probes are spectroscopically active and unsaturated coordination metal complexes, such as ruthenium-pyridyl complexes, ruthenium-phenanthroline complexes, or the like. These spectroscopic probes bind to one or more exposed coordination sites in non-native conformations of a metalloprotein. These exposed coordination sites generally are bound to specific amino acid ligands in the native protein, but become open to coordination by the small molecular probe in non-native states of the metalloprotein.

Other spectroscopic systems utilizing spectroscopic probes also can be utilized in embodiments of the invention, such as fluorescence systems based on FRET (fluorescence resonance energy transfer) and PET (photo-induced electron transfer), such as those disclosed in U.S. Pat. No. 6,011,984, and the like, which is incorporated by reference in its entirety herein.

ii) Survival Curve Analysis of the Physical Status of a Protein Formulation: The Second Step in the Accelerated Physical Stability Method After gathering spectroscopic data reflective of the physical stability of one or more protein formulations, these data are compared using survival curve analyses. These survival curve analyses are statistical methods similar to those that have been used in the prior art, for example, in the analysis of data from clinical trials of a new pharmaceutical drug. In these clinical trials the survival of patients taking the drug is compared to the survival of patients taking a placebo or another drug. Thus, at the end of the trial, a percent survival is obtained for each patient population. As with any statistical method, the number of individuals, or samples, i.e., an N value, must be chosen to yield statistically significant results. In an embodiment of the invention that utilizes a 96 well microplate, as described below, the N value chosen is preferably about 16 to about 48 identical sample formulations with an N value of about 24 identical samples being most preferred. Other N values also may be used depending of the size of the microplate utilized, or other similar device for containing the samples.

In preferred embodiments of the invention, the survival curve analysis compares the rate of protein aggregation of a first sample type, containing a statistically relevant number of identical samples of a particular insulin formulation, to that of one or more samples types containing a statistically relevant number of identical samples of different insulin formulations. In particular embodiments of the invention, protein aggregation, or changes in protein conformation, is equated with non-survival of the protein.

A protein reference batch of known physical stability can be used to estimate the physical stability of particular unknown insulin formulations. A comparison to a reference protein batch controls for small changes in starting conditions that can affect the absolute rate of aggregation, as well as controlling drift in the light source intensity and detector sensitivity. These small changes and drifts can affect the absolute intensity measurements Additionally, the possibility of dye bleaching by incident radiation can be addressed by using a protein reference batch. Thus, the use of a protein reference batch controls for random variables in the experimental protocol.

However, a protein reference batch is not necessary to the evaluation of the relative physical stability of a series of protein formulations. In this experimental design, each protein formulation acts as a reference to the other protein formulations under evaluation. Thus, the relative physical stability of a series of protein formulations can be determined without the use of a protein reference batch.

In particular embodiments of the inventive method, the median survival time for particular protein samples to reach a state where 50% of the protein is in an aggregated state, or 50% of the protein has not survived, is chosen as an end point of the experimental run. This end point is preferred as a metric and appears to adequately represent the physical stability of a given protein formulation. In other embodiments of the invention, other points on the survival curve can be used as a metric of the physical stability of the protein formulations under evaluation. The median survival, however, appears to represent and coincide with the average physical stability of the sample formulations Thus in embodiments of the invention, the longer the median survival, the greater is the physical stability of the protein formulations under evaluation.

In embodiments of the invention, a survival curve analysis of the change in physical state of a particular protein is necessary because direct evaluation of the physical stability of protein formulations is difficult, to nearly impossible, to obtain simply from a profile of protein aggregation versus time. There are two main reasons for this difficulty. The first reason is experimental. The raw data, as shown in FIG. 1 for several insulin formulations, are very noisy mostly due to a stirring device, such as Teflon bead, being in the light path of the fluorometer, as described below. The second reason is that the kinetics of aggregation is not well understood. For insulin, it has been proposed that the process of aggregation is autocatalytic.[2] The actual reaction mechanism of aggregation of insulin, which includes fibril formation, however, is largely unknown. Accordingly an analytical solution to the aggregation kinetic mechanism of insulin is also unknown.

[2]Sluzky, V., Tamada, J. A., Klivanov, A. M., and Langer, R. *Proceedings of the National Academy of Science*, 1991, 88 p. 9377.

The use of a survival curve analysis applied to the spectroscopic data of changes in protein states yields a simple method which compares a statistically relevant number of samples of a given formulation to a statistically relevant number of samples of another formulation, yielding a relative physical stability profile of the sample types under evaluation. Accordingly, no prior knowledge or understanding of the mechanism of aggregation, or the mechanism of protein conformational changes, is needed for applications of embodiments of the invention.

Once aggregation profiles are obtained for each sample type under evaluation, as shown in FIG. 1, a calculation of the time to reach a certain fluorescence level is performed. This time to reach a certain fluorescence level is generally set at 50% survival, but can vary with the needs of particular experiments. This end point of the survival analysis represents a point in the aggregation profile that is at least beyond the initiation of aggregation. Moreover, the level of fluorescence obtained at the 50% survival point was determined to yield reliable results. This level of fluorescence is generally substantially greater than the background noise of the system and ensures that the results are statistically relevant. For experimental systems with greater or less noise, higher or lower levels of fluorescence can be set as end points.

The data now consist of a series of times to the initiation of aggregation. Once the time to start aggregation is calculated, a standard Kaplan-Meier survival curve analysis[3], where survival fractions are calculated as a function of time, is applied. For a comparison between the formulations of interest and a reference batch, for example, the log rank test equivalent to the Mantel-Haenszel test is performed. This test generates a P value testing the null hypothesis that the survival curves are identical

[3]Campbell, M. and Machin, D., *Medical Statistics*, Wiley, New York, 1983. p. 112.

Other important information that can be obtained from comparing two survival curves is their median survival and the ratio of the median survival of a reference batch, or other protein sample type, to the median survival of the sample type of interest. Median survival, as described above, is the time for 50% of the samples to reach a pre-determined level of fluorescence. If the samples do not show fluorescence at the end of the experiment, then median survival cannot be computed and we can only estimate a "minimum" median survival.

iii) A Preferred Embodiment of the Accelerated Physical Stability Method of the Invention Embodiments of the present invention are directed to methods of evaluating the physical stability of protein formulations, particularly insulin formulations. These methods generally involve the steps outlined above. In the following description, the physical stability of particular insulin formulations are evaluated using a preferred embodiment of the accelerated physical stability method of the invention. However, the accelerated physical stability methods of the embodiments of the invention can be used to evaluate any protein that undergoes a change in conformation due to an application of a controlled stress.

The first step is to physically stress the insulin formulations under evaluation by controlled agitation. A series of identical insulin samples are prepared to yield a first sample type, or reference batch in this example, and another series of identical insulin samples are prepared to yield a second sample type. A small volume of each insulin sample is placed in an open well, i.e., exposed to air, of a 96-well microplate. One or more small, stirring device(s), preferably in the form of Teflon (polytetrafluoroethylene) bead(s), is also placed in each sample well. The Teflon bead has a very hydrophobic surface, which increases the interfacial tension within each well. However, the stirring device can be made of different materials, including hydrophilic materials A dye, Thioflavin-T, is then added to each sample well. Thioflavin-T has been shown[4] to bind to aggregated protein states.

[4]Levine, H., *Protein Science*, 1993, 2, p. 404

Although this particular embodiment of the invention exposes the protein formulations to air, and thus increasing the interfacial tension, i.e., exposure to a air-water interfaces, other embodiments of the invention utilize placing the protein samples in sealed vials from which residual air is evacuated, thereby reducing the air-water interface.

In this particular embodiment of the invention, the physical stress applied is agitation of the microplate in a commercial instrument that also measures the fluorescence of Thioflavin-T as a function of the time of agitation. A typical instrument suitable for use in the accelerated physical stability methods of the invention is a Fluorskan fluorescence plate reader (Lab-systems). In this embodiment, the plate is orbitally agitated. However other forms of agitation, such as shaking and vibrating, are suitable for use in other embodiments of the invention. After a certain time of agitation, a curve is generated, as shown in FIG. 1, which is a plot of aggregation, as measured by the increase in Thioflavin-T fluorescence intensity, as a function of time. The data generated are then subjected to a survival curve analysis.

In this particular experiment using an embodiment of the accelerated physical stability method of the invention, the experiment begins by adding approximately 200 microliters of a given protein formulation into multiple wells in the 96-well microplate. A single Teflon bead is added to the well together with an aliquot of Thioflavin-T dissolved in water The microplate is covered with a Mylar sheet to reduce evaporation and avoid against accidental particulate contamination. The covered microplate is then placed in an incubated orbital shaker and is agitated with a controlled force. The preferred operational parameters are given in the Table 1.

Table 1: Operational Parameters for Protein Stability Estimation

Sample volume: 150–250 µl preferably 190 µl

Thioflavin-T: 10–30 µM, preferably 20 µM

Shaking speed: 480–1200 rpm, preferably 960 rpm

Shaking diameter: 1–5 mm, preferably 1 mm

Temperature: 25–40° C., preferably 37° C.

Microplate cover: 1–3 sheets of Mylar covers preferably one sheet.

Excitation wavelength: 440 nm–500 nm, preferably about 444 nm

Emission wavelength: 480 nm–520 nm, preferably about 510 nm

Measurement directions: top down

Number of wells per formulation: $\geq 24$

Run time: 3–9 days or until more than 50% of the samples start to aggregate

A representative snap shot of an aggregation profile for a single run using all 96 wells is shown FIG. 1. This snap shot gives the observer a quick look at the experimental results without any further analysis. As can be observed form inspection of the snap shot in FIG. 1, some samples are fully aggregated, such as samples A1, A2, A8, A9 and A10, some samples are partially aggregated, such as G1 and H1, and some samples are not aggregated at all, such as A11 and B3. A snap shot is taken at every measurement during the entire run. Once an aggregation profile is obtained, the time to reach a certain fluorescence level (e.g. 50) is calculated, which in this example represents the definite initiation of aggregation. The particular fluorescence level can be determined from a comparison to the background noise to ensure that the fluorescence level chosen is above the background noise.

Once the time to start aggregation is calculated (e.g. $t_{50}$) then we can plot a survival curve, where survival fractions are calculated using Kaplan-Meier method. An example of a survival curve is shown in FIG. 2. These calculations are performed using commercially available software, such as Prism or an equivalent software. Further examples are given below.

iv) Conclusions

Embodiments of the accelerated physical stability method of the invention have several advantages compared to other prior art tests. One of the most significant advantages is speed. This method typically aggregates proteins very quickly which allows faster screening of formulations. Another advantage is that the method uses less volume than many other prior art methods. Embodiments of the invention, therefore, are time-efficient and cost-efficient allowing the user to test many samples at once. Testing many samples at the same time also can increase the statistical significance of the test results. Another advantage of embodiments of the invention is that there is no requirement to understand the reaction mechanism of protein instability, i.e., the mechanism that underlies a change in the conformation of the protein of interest, to evaluate the relative physical stability of a series of protein formulations. Finally, embodiments of the invention are fully automated data monitoring systems that allow the user to monitor fluorescence at user-defined intervals and gives a complete aggregation profile for all wells used.

In summary, novel methods to estimate or evaluate the physical stability of insulin and other protein drug formulations are developed. A preferred embodiment of the invention is one where the proteins of interest show aggregation behavior. However, other embodiments of the invention do not require aggregation, but only a change in the native conformation of a protein of interest and a spectroscopic probe of this structural change. Specific embodiments of the invention involves essentially two steps. The first step of the preferred embodiment involves the rapid aggregation (or change in conformation) of a small volume of sample in each well of a well plate, together with fully automated monitoring of aggregation-specific fluorescence. The second step of the preferred embodiment includes an analysis of the plots of fluorescence versus time followed by a Kaplan-Meier survival curve analyses and calculations of the appropriate median survival and median survival ratios. The use of embodiments of the invention rapidly and reproducibly yield the relative physical stability of different formulations under evaluation.

EXAMPLES

The detailed protocols given below are not to be construed as necessary to the methods of the invention. Sample preparation, instrumentation, materials, or the like, are given as examples of how to carry out embodiments of the invention.

Example 1

An example of the calculations using Prism software, for example, is as follows. In the X columns, the times to start aggregation (e.g. $t_{50}$) are entered. If a particular sample did not aggregate, the time when the run ended is entered. In the Y columns, the number 1 is entered for the rows where the sample aggregated and 0 for the rows where the sample did not aggregate at a given time. Thus, using this method, a calculation of the survival fractions at each data collection time point and survival fraction vs. time are generated. For comparison between the formulation of interest and the reference batch, the log rank test, which is equivalent to the Mantel-Haenszel test, is performed. This test generates a P value testing the null hypothesis that the survival curves are identical in the overall populations. In general if the P value is less than 0.05, the difference between the two sets of data being compared are statistically significant. In other words, the physical stability of the two formulations is significantly different. Other information that can be obtained from comparing two survival curves is the median survival and its ratio. Median survival is the time at which half the samples have aggregated, more specifically, the time at which half the samples reached a fluorescence value of 50 in intensity (arbitrary units). If survival exceeds 50% at the longest time points, then median survival cannot be computed. Prism calculates median survival and also the ratio of the median survival along with its 95% confidence interval.

Example 2

The example, shown in FIG. 2, is a graphic display of the experimental data of % survival. The statistical evaluation of the data was performed using commercial software (GraphPad). A comparison of the survival curve statistical data of the plot shown in FIG. 2 is shown in Table 2.

TABLE 2

Illustration of Typical Survival Curve Data

Log rank Test

| | |
|---|---|
| Chi square | 56.46 |
| df | 1 |
| P value | P < 0.0001 |
| P value summary | *** |
| Are the survival curves sig different? | Yes |

Median survival

| | |
|---|---|
| HRI-A2 | 164.1 hrs |
| syk-1 | 40.08 hrs |
| Ratio | 4.094 |
| 95% CI of ratio | 3.526 to 4.662 |

Based on the above information, it is concluded that the difference in the estimated relative physical stability of the two formulations under evaluation is statistically significant and that the median time to a fixed fluorescence is approximately 4 times longer for HRI-A2 as for syk-1. When the same set of sample types were repeatedly tested, the statistical error or standard deviation of the median survival ratio is between 11 and 20% (see Examples 3 and 4 below).

Example 3

In this example, three experimental runs were conducted to validate the accelerated physical stability method, referred to as Val 6, Val 7 Val 8 (n=3). In these experimental runs, there are 48 samples per sample type (N=48). Each experimental run compares two formulations, one formulation using Diosynth semi-synthetic insulin and the other formulation using Aventis semi-synthetic insulin. Table 3 gives the composition of the protein formulations compared. FIG. 3 shows survival curve analyses for the three runs. Table 4 gives the survival curve analysis for the three different runs.

TABLE 3

Formulation Summary

| | syk-1 | 1196 |
|---|---|---|
| insulin type | semi-synthetic | Semi-synthetic |
| insulin manufacturer | Diosynth | Aventis |
| insulin concn (units/ml) | 400 | 400 |
| Tris (mg/ml) | 6 | 6 |
| glycerin (mg/ml) | 17 | 17 |
| phenol (mg/ml) | 2.7 | 2.7 |
| surfactant type | Genapol PF10 | Genapol PF10 |
| surfactant concn (mg/ml) | 0.01 | 0.01 |
| zinc (mg/ml) | 0.108 | 0.108 |

TABLE 4

Survival Curve Analysis

| Test # | insulin sample | median survival (hr) | median survival ratio (X vs. syk-1) | % survival at the end of run |
|---|---|---|---|---|
| Val 6 | syk-1 | 38.55 | 1.00 | 0.00 |
|  | Aventis Lot 1196 | 24.88 | 0.65 | 6.25 |
| Val 7 | syk-1 | 28.01 | 1.00 | 0.00 |
|  | Aventis Lot 1196 | 22.78 | 0.81 | 0.00 |
| Val 8 | syk-1 | 50.00 | 1.00 | 2.08 |
|  | Aventis Lot 1196 | 37.53 | 0.75 | 16.67 |
|  |  | average | STD | % STD |
| median survival ratio | 1196 vs. syk-1 | 0.74 | 0.08 | 11.51% |
| median survival | 1196 | 28.40 | 7.98 | 28.10% |
|  | syk-1 | 38.85 | 11.00 | 28.31% |

Example 4

Figure 4:
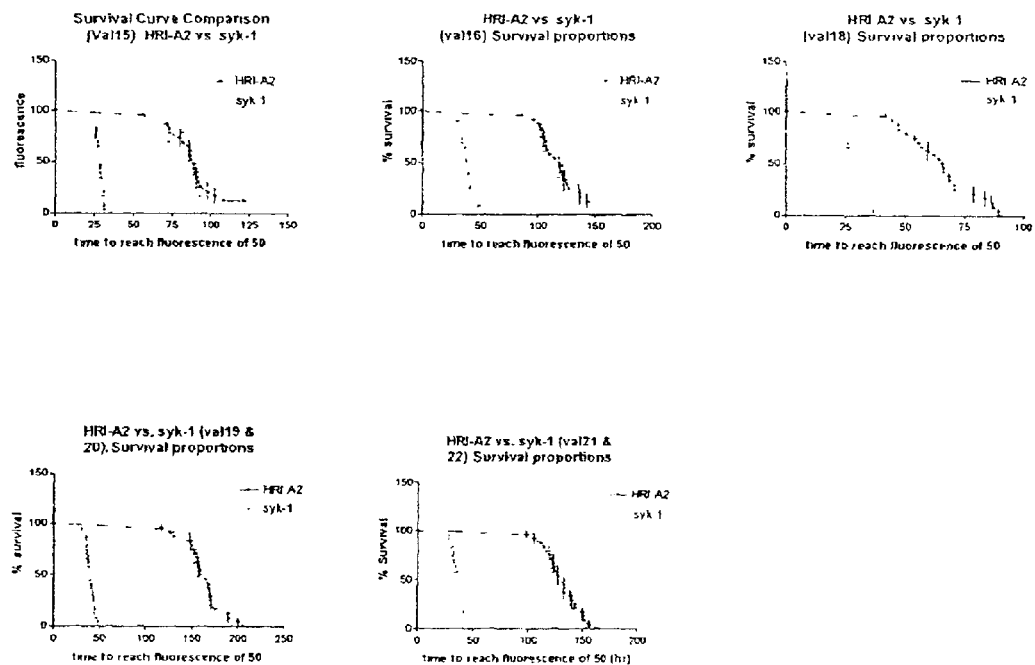
FIG. 4 is a graphic representation of a survival curve comparison of five experimental runs which further validate embodiments of the present invention.

In this example, five experimental runs were conducted to further validate the accelerated physical stability method (n=5). These are referred to as Val 15, Val 16, Val 18, Val 19 and Val 20. In these experimental runs, there are 24 samples per sample type (N=48). Each experimental run compares two formulations. One formulation, referred to as syk-1 is used as a reference protein batch in each of the five experimental runs. Table 6 gives the composition of the protein formulations compared, i.e., the reference protein batch versus a surfactant-stabilized formulation. Table 5 gives the formulation summary of the protein formulations under evaluation. Table 6 gives the data for the survival curve analyses for the five runs. FIG. 4 shows a plot of the survival curve analyses for the five runs.

TABLE 5

Formulation Summary

|  | syk-1 | HRI-A2 |
|---|---|---|
| insulin type | semi-synthetic | Human Recombinant |
| insulin manufacturer | Diosynth | Diosynth |
| insulin concn (units/ml) | 400 | 400 |
| Tris (mg/ml) | 6 | 6 |
| glycerin (mg/ml) | 17 | 17 |
| phenol (mg/ml) | 2.7 | 2.7 |
| surfactant type | Genapol PF10 | Genapol PF10 |
| surfactant concn (mg/ml) | 0.01 | 0.01 |
| zinc (mg/ml) | 0.108 | 0.108 |

TABLE 6

Survival Curve Analysis

| Test # | insulin sample | median survival (hr) | median survival ratio (X vs. syk-1) | % survival at the end of run |
|---|---|---|---|---|
| Val 15 | syk-1 | 28.70 | 1.00 | 0.00 |
| (122 hrs) | HRI-A2 | 88.65 | 3.09 | 13.04 |
| Val 16 | syk-1 | 38.59 | 1.00 | 0.00 |
| (144 hrs) | HRI-A2 | 118.10 | 3.06 | 12.50 |
| Val 18 | syk-1 | 27.66 | 1.00 | 0.00 |
| (138 hrs) | HRI-A2 | 65.82 | 2.38 | 0.00 |
| Val 19 & 20 | syk-1 | 40.08 | 1.00 | 0.00 |
| (213 hrs) | HRI-A2 | 164.10 | 4.09 | 0.00 |
| Val 21 & 22 | syk-1 | 36.55 | 1.00 | 0.00 |
| (237 hrs) | HRI-A2 | 132.70 | 3.63 | 0.00 |
|  |  | average | STD | % STD |
| median survival ratio | HRI-A2 vs. syk-1 | 3.25 | 0.65 | 19.91% |
| median survival | HRI-A2 | 113.87 | 38.21 | 33.56% |
|  | syk-1 | 34.32 | 5.75 | 16.76% |

III. Surfactant-Stabilized Protein Formulations Derived From an Embodiment of the Accelerated Physical Stability Method of the Invention Maintaining the native and biologically active, three-dimensional structure of insulin is critical to preserving the biopotency of a particular insulin formulation. Heat, chemicals, mechanical stress and surface interactions, especially interactions of insulin with hydrophobic surfaces, can destroy the structural integrity of the protein. Moreover, the delivery of insulin via infusion pumps provides a source of thermo-mechanical energy that may be disruptive to the native structure of insulin. This thermo-mechanical energy is imparted to insulin and can result in denaturation and subsequent aggregation of the protein, as well as protein precipitation. These changes in the physical state of the insulin can cause flow impeding occlusions in infusion devices. Additionally, infusion devices introduce insulin to destabilizing hydrophobic interfaces that are found at the surfaces of the pump reservoirs and delivery catheters of these devices. These interactions of insulin with the hydrophobic surfaces of infusion devices add to the physical stress placed on insulin during delivery to a patient. Further, since any pharmaceutical process for the production of insulin includes a time lag between its production and delivery to an appropriate patient, an insulin formulation also must be stable over this time period.

To assist in maintaining the biologically active structure of insulin, various excipients are generally added as stabilizing excipients. Surfactants represent one class of stabilizing excipients. However, a considerable amount of time and resources generally is required to evaluate whether a particular surfactant will have a stabilizing effect on a particular protein formulation. Additionally in the pharmaceutical industry, a major concern is ease of approval from the regulatory body controlling licensing of pharmaceutical products.

In the case of insulin, a common physical stability problem is protein aggregation or fibril formation. A model for insulin fibrillation has been proposed where the early stages of insulin fibril formation involve the dissociation of native associated states, i.e., the insulin hexamer, the insulin tetramer and the insulin dimer, to yield a native monomer, which is in equilibrium with a fibrillation-component partially folded intermediate. This intermediate then oligomerizes to form transient soluble oligomers that lead to the formation of a nucleus. In the absence of physical stress, e.g., vigorous agitation, the equilibrium will favor the associated native states. However, in the presence of significant interfacial interactions, the equilibrium will shift in favor of the intermediate. Once formed, the intermediate has a strong propensity to oligomerize to form biologically inactive insulin fibrils.

Without being held to a particular theory of surfactant stabilization of insulin, it is hypothesized that a surfactant-stabilized insulin formulation gains greater physical stability to aggregation or fibril formation from interactions of an appropriate surfactant with a partially unfolded insulin monomer. Further, it is hypothesized that an appropriate surfactant prevents non-specific aggregation of insulin and correct refolding of the denatured portions of the molecule, thus further stabilizing the formulation to aggregation and fibril formation.[5] Thus, an appropriate surfactant is hypothesized to mimic the role of molecular chaperones, which are a class of naturally occurring protein molecules that catalyze correct folding and prevent nonspecific aggregation of newly synthesized proteins in a cell.

[5]Jones, L., Bam, N. and Randolph. T. "Surfactant-Stabilized Protein Formulations" in Therapeutic Protein and Peptide Formulations and Delivery, 1997, Chapter 12, p. 206, American Chemical Society Publication.

Non-ionic surfactants are amphiphatic molecules which generally include a bulky polar head group attached to a hydrophobic chain. The chemical structure of non-ionic surfactants that have been approved for use in the pharmaceutical industry are given in FIG. 5. Some of these chemical structures are characterized by a polydispersity in the hydrophobic chain lengths, which affects the critical micellar concentration (CMC). In developing novel surfactant-stabilized formulations, a good starting point is to use a surfactant concentration near the CMC because it is near or at this concentration range that properties such as interfacial tension are affected greatly. However, with some protein formulations, an optimal surfactant concentration may be one that is greater than the CMC, as was observed with the protein rhodanese, a non-membrane associated protein found in the mitochrondria. Moreover, CMCs are not a constant, but are dependent on a host of formulation factors, such as ionic strength, pH, and the presence of other excipients in the particular protein formulation.

Despite a general use of surfactants in the pharmaceutical industry, particular protein formulations must be evaluated to ascertain whether a particular surfactant actually stabilizes, or destabilizes, a protein formulation. Thus, an embodiment of the accelerated physical stability method of the present invention was used to evaluate the physical stability of certain insulin formulations that include a surfactant. The surfactants tested are non-ionic and government regulatory approved excipients.

The surfactant-stabilized insulin formulations of embodiments of the present invention have been shown to have a high degree of physical stability as compared to prior art, surfactant-stabilized insulin formulations, such as insulin formulations containing the surfactant Genapol PF-10. The high degree of physical stability exhibited by the insulin formulations of embodiments of the present invention was discovered in a time-efficient and cost-efficient manner using an embodiment of the accelerated physical stability method disclosed above. Thus, the surfactant-stabilized insulin formulations of the embodiments of the present invention have a longer median survival under the physical stress of agitation imposed in an embodiment of the accelerated physical stability method of the invention. However, the superior physical stability of the novel protein formulations of embodiments of the invention can be demonstrated using prior art formulation physical stability tests.

The insulin formulations of embodiments of the present invention are advantageous in the pharmaceutical production and distribution of insulin. Moreover, given that the high physical stability of these surfactant-stabilized insulin formulations was discovered using an embodiment of the accelerated physical stability method of the invention that imposes both mechanical stress and interfacial tension on a given formulation demonstrates that these novel formulations are particularly suitable for use with infusion delivery devices, such as external and implantable insulin pumps, or the like. Both external and implantable insulin pumps are potentially disruptive to the physical stability of a particular insulin formulation due to the combined effects of heat, mechanical stress and exposure to hydrophobic surfaces. Thus, the surfactant-stabilized insulin formulations of embodiments of the present invention can greatly compensate for the potentially adverse conditions presented to insulin during delivery via external or implantable pump therapy.

The surfactant-stabilized insulin formulations of embodiments of the present invention include at least insulin, a buffer system, an isotonicity agent, a preservative, metal ions, and a non-ionic surfactant. The preferred non-ionic surfactants suitable for use in embodiments of the present invention are government regulatory approved polysorbate surfactants, such as Tween 20, Tween 40, Tween 60 and Tween 80, poloxyethylene ether surfactants, such as Brij 35, polyethylene glycol ether surfactants, such as Triton X-100 and Triton X-114, and mixtures of these surfactants, preferably in a concentration range of about 0.001 mg/ml to about 0.1 mg/ml, most preferably about 0.02 mg/ml to about 0.04 mg/ml. The chemical structures of representative non-ionic surfactants for use in embodiments of the present invention are shown in FIG. 5.

The surfactant-stabilized insulin formulations of embodiments of the invention are superior in physical stability to the same insulin formulation except that the added surfactant is a polypropylene glycol/polyethylene glycol block copolymer, i.e., a Genapol surfactant. Previously, it has been reported that Genapol type surfactants, particularly Genapol PF-10 at concentrations of 0.001% (w/v), dramatically stabilizes insulin over a wide range of protein concentrations as compared with the same formulation without Genapol. The mechanism of stabilization of insulin by Genapol was proposed to be competitive binding of Genapol to hydrophobic surfaces. Thus, insulin is inhibited from binding to these surfaces. Accordingly, insulin unfolding and denaturation, which occurs from the interaction with hydrophobic surfaces, is substantially prevented. The surfactant-stabilized insulin formulations of the present invention possess superior physical stability to that of a Genapol-stabilized insulin formulation, and therefore, can be characterized as providing an even more dramatic effect on insulin stabilization over a wide protein concentration range.

The insulin formulations of embodiments of the invention may include any insulin, such as human or animal insulins, recombinant insulins, semi-synthetic insulins, insulin analogues, insulin derivatives and mixtures of these insulins. The preferred insulins for use in the surfactant-stabilized insulin formulations of the invention is human insulin, as well as human recombinant insulin. The insulin concentration range for embodiments of the formulations of the invention is preferably about 2 U/ml to about 1000 U/ml, most preferably, about 400 U/ml.

Once the desired insulin concentration is determined, the remaining components of the embodiments of the insulin formulations can be varied, i.e., other than insulin at the predetermined concentration, so that the final composition of a particular embodiment yields a physical stability reflected in a mean survival time, using an embodiment of the accelerated physical stability method of the invention, that is greater than a Genapol PF-10 stabilized formulation, when compared to the same formulation stabilized instead by a polysorbate, a poloxyethylene ether, a polyethylene glycol ether, and mixtures of these surfactants.

A buffer system suitable for use in embodiments of the invention is any buffer system that enables the surfactant-stabilized insulin formulation to achieve a mean survival time, using an embodiment of the accelerated physical stability method of the invention, that is greater than a Genapol PF-10 stabilized formulation, when compared to the same formulation stabilized instead by a polysorbate, a poloxyethylene ether, a polyethylene glycol ether, and mixtures of these surfactants. Specific buffer systems suitable for use in the surfactant-stabilized insulin formulations are a Tris buffer system, a phosphate buffer system, a glycine buffer system, a glyclyglycine buffer system, acetic acid buffer system, and mixtures of these buffers, or the like. Also suitable for use in embodiments of the invention are the mixed buffer systems disclosed in U.S. patent application Ser. No. 09/733,738, which is hereby incorporated by reference in its entirety. In embodiments of the invention, a preferred buffer system for use in particular embodiments of the invention is a Tris buffer, preferably in a concentration range from about 4 mg/ml to about 10 mg/ml, most preferably 6 mg/ml. The preferred pH range for a Tris buffer system is about pH 7.0 to about pH 7.8.

An isotonicity agent suitable for use in embodiments of the invention is any isotonicity agent that enables the surfactant-stabilized insulin formulation to achieve a mean survival time, using an embodiment of the accelerated physical stability method of the invention, that is greater than a Genapol PF-10 stabilized formulation, when compared to the same formulation stabilized instead by a polysorbate, a poloxyethylene ether, a polyethylene glycol ether, and mixtures of these surfactants. Specific isotonicity agents suitable for use in the surfactant-stabilized insulin formulations are glycerol or glycerin, sodium chloride, glucose, mannitol, sucrose, dextrose, lactose and mixtures of these isotonicity agents. In embodiments of the invention, a preferred isotonicity agent is glycerin, preferably in a concentration range of about 14 mg/ml to about 20 mg/ml, and most preferably about 16–17 mg/ml.

A preservative suitable for use in embodiments of the invention is any preservative that enables the surfactant-stabilized insulin formulation to achieve a mean survival time, using an embodiment of the accelerated physical stability method of the invention, that is greater than a Genapol PF-10 stabilized formulation, when compared to the same formulation stabilized instead by a polysorbate, a poloxyethylene ether, a polyethylene glycol ether, and mixtures of these surfactants. Specific preservatives suitable for use in the surfactant-stabilized insulin formulations are phenol, m-cresol, chlorocresol and mixtures of these preservatives. In embodiments of the invention, a preferred preservative is phenol, preferably in a concentration range of about 1 mg/ml to about 3 mg/ml, and most preferably about 2.7 mg/ml. Optionally, m-cresol also can be used in addition to phenol in the surfactant-stabilized insulin formulations, preferably in a concentration range up to about 2.2 mg/ml.

Metal ions suitable for use in embodiments of the invention are zinc ions, cobalt ions, manganese ions, calcium ions, magnesium ions and mixtures of these metal ions. In certain surfactant-stabilized insulin formulations of the invention that include an insulin known to exist largely in a monomer form, such as LISPRO insulin, the addition of metal ions to the formulation of the invention is optional. In embodiments of the invention, the preferred metal ion is zinc, preferably in a concentration range of about 90 mg/ml to 120 mg/ml, and most preferably about 100 mg/ml to about 110 mg/ml.

CONCLUSION

Novel surfactant-stabilized insulin formulations were developed using an embodiment of the accelerated physical stability method of the present invention. These surfactant-stabilized insulin formulations demonstrate superior physical stability when compared to Genapol PF-10 stabilized insulin formulations. These novel insulin formulations are especially suite for use in implantable, as well as external, infusion systems for insulin delivery.

EXAMPLES

In the following examples, experimental runs were performed using an embodiment of the accelerated physical stability method disclosed above. In these examples, experiments were performed as described in Examples 1–4 shown above. The detailed protocols given below are not to be construed as necessary to the methods of the invention. Sample preparation, instrumentation, materials, or the like, are given as examples of how to carry out embodiments of the invention.

Example 5

In this example, two non-ionic surfactants were compared to Genapol PF-10. Table 7 details the composition of the tested sample types. Table 8 gives the details of the survival curve analysis for each tested formulation or sample type.

TABLE 7

Formulation Summary

| | syk-1 | HRI-A2 | HRI-PEG | HRI-TW80 |
| --- | --- | --- | --- | --- |
| insulin type | semi-synthetic | human recombinant | human recombinant | human recombinant |
| insulin manufacturer | Diosynth | Diosynth | Diosynth | Diosynth |
| insulin concn (units/ml) | 400 | 400 | 400 | 400 |
| Tris (mg/ml) | 6 | 6 | 6 | 6 |
| glycerin (mg/ml) | 17 | 17 | 17 | 17 |
| phenol (mg/ml) | 2.7 | 2.7 | 2.7 | 2.7 |
| surfactant type | Genapol PF10 | Genapol PF10 | PEG 250 | Tween80 |
| surfactant concn (mg/ml) | 0.01 | 0.01 | 0.04 | 0.04 |
| zinc (mg/ml) | 0.108 | 0.108 | 0.108 | 0.108 |

TABLE 8

Survival Curve Analysis

| Test # | insulin sample | median survival (hr) | median survival ratio (X vs. syk-1) | % survival at the end of run |
|---|---|---|---|---|
| Val 18 (138 hrs) | syk-1 | 27.66 | 1.00 | 0.00 |
| | HRI-A2 | 65.82 | 2.38 | 0.00 |
| | HRI-TW80 | undefined (>138) | ND (>4.99) | 70.83 |
| | HRI-PEG | 39.96 | 1.45 | 0.00 |

Figure 6:
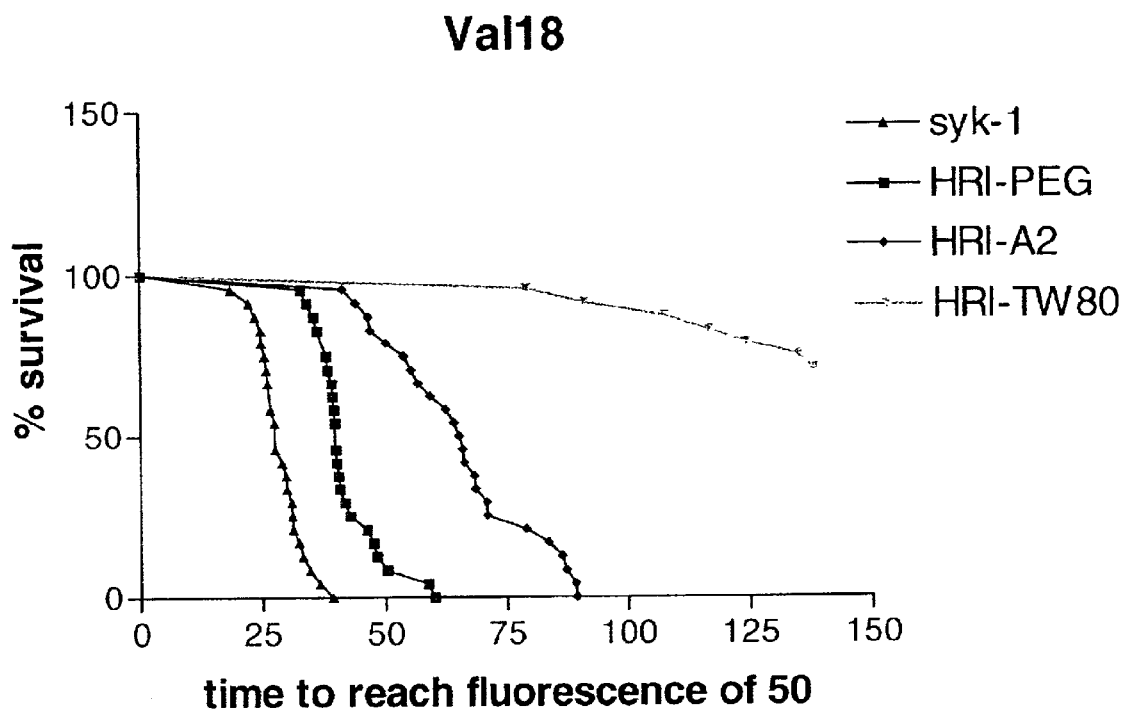
FIG. 6 is a graphic representation of a survival curve comparison of three surfactants for use with insulin formulations of the present invention; the surfactants compared are Genapol PF-10, PEG and Tween 80.

In this experiment, a polyethylene glycol (PEG 250) formulation, referred to as HRI-PEG, a polysorbate (Tween 80) formulation, referred to as HRI-TW80, were compared to a Genapol PF-10 formulations, referred to as HRI-A2, to evaluate the ability of each of these surfactants to stabilize a human recombinant insulin formulation. In this experiment, these three formulations were compared to a reference batch which included a semi-synthetic insulin and Genapol PF-10, referred to as syk-1. The results of this experimental run are graphically depicted in FIG. 6.

Example 6

Another experiment was performed comparing the HRI-A2, containing Genapol PF-10, to HRI-TW80, containing Tween 80, and HRI-TW20, containing Tween 20, in terms of relative physical stability of these three formulations. Table 9 gives the details of the composition of each tested formulation. Table 10 gives the details of the survival curve analysis for each tested formulation.

TABLE 9

Formulation Summary

| | syk-1 | HRI-A2 | HRI-TW80 | HRI-TW20 |
|---|---|---|---|---|
| insulin type | semi-synthetic | human recombinant | human recombinant | human recombinant |
| insulin manufacturer | Diosynth | Diosynth | Diosynth | Diosynth |
| insulin concn (units/ml) | 400 | 400 | 400 | 400 |
| Tris (mg/ml) | 6 | 6 | 6 | 6 |
| glycerin (mg/ml) | 17 | 17 | 17 | 17 |
| phenol (mg/ml) | 2.7 | 2.7 | 2.7 | 2.7 |
| surfactant type | Genapol PF10 | Genapol PF10 | PEG 250 | Tween80 |
| surfactant concn (mg/ml) | 0.01 | 0.01 | 0.04 | 0.04 |
| zinc (mg/ml) | 0.108 | 0.108 | 0.108 | 0.108 |

TABLE 10

Survival Anaylsis

| Test # | insulin sample | median survival (hr) | median survival ratio (X vs. syk-1) | % survival at the end of run |
|---|---|---|---|---|
| Val 19 & 20 (213 hrs) | syk-1 | 40.08 | 1.00 | 0.00 |
| | HRI-A2 | 164.10 | 4.09 | 0.00 |
| | HRI-TW80 | 168.10 | 4.20 | 0.00 |
| | HRI-TW20 | 161.80 | 4.04 | 0.00 |

Figure 7:
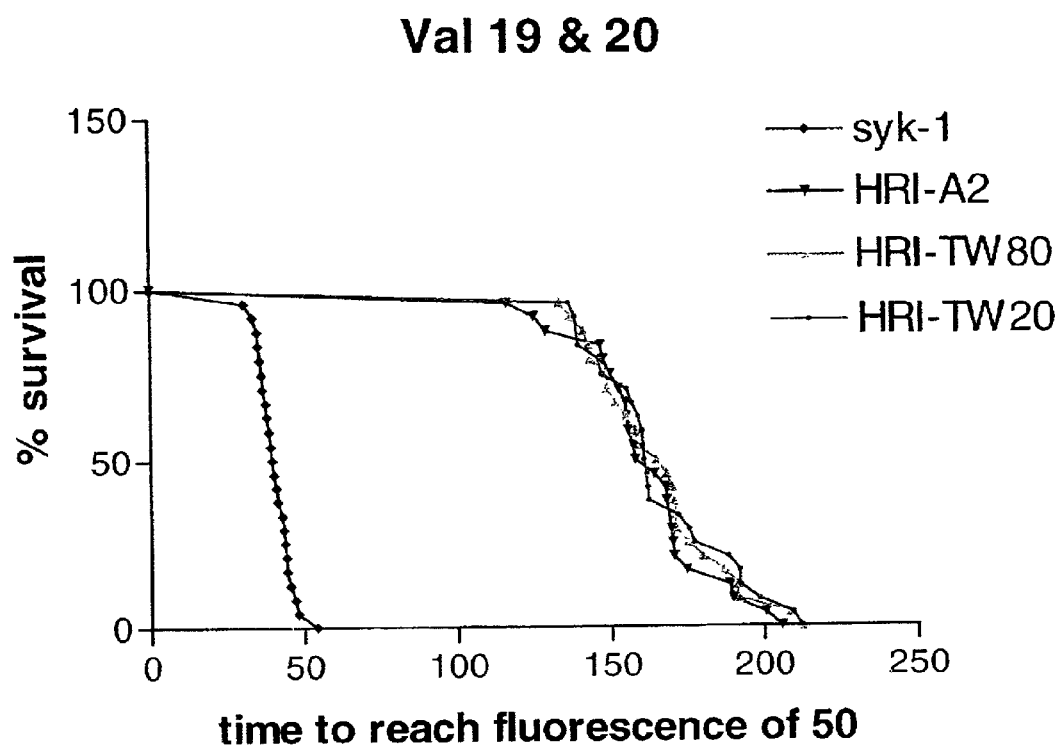
FIG. 7 is a graphic representation of a survival curve comparison of three surfactants for use with insulin formulations of the present invention; the surfactants compared are Genapol PF-10, Tween 20 and Tween 80.

In this experimental run, these three formulations were compared to the reference batch, syk-1, which included a semi-synthetic insulin and Genapol PF-10, to evaluate the ability of these surfactants to stabilize the tested insulin formulations. The results of this experiment are graphically depicted in FIG. 7.

Example 7

Another experiment was performed comparing the HRI-A2, containing Genapol PF-10, to HRI-BJ-35, containing Brij 35, and HRI-TX-100, containing Triton X-100, in terms of relative physical stability of these three formulations. Table 11 gives the details of the composition of each tested formulation. Tables 12 gives the details of the survival curve analysis for each tested formulation.

TABLE 11

Formulation Summary

| | syk-1 | HRI-A2 | HRI-BJ-35 | HRI-TX-100 |
|---|---|---|---|---|
| insulin type | semi-synthetic | human recombinant | human recombinant | human recombinant |
| insulin manufacturer | Diosynth | Diosynth | Diosynth | Diosynth |
| insulin concn (units/ml) | 400 | 400 | 400 | 400 |
| Tris (mg/ml) | 6 | 6 | 6 | 6 |
| glycerin (mg/ml) | 17 | 17 | 17 | 17 |
| phenol (mg/ml) | 2.7 | 2.7 | 2.7 | 2.7 |
| surfactant type | Genapol PF10 | Genapol PF-10 | Brij 35 | Triton X-100 |
| surfactant concn (mg/ml) | 0.01 | 0.01 | 0.04 | 0.04 |
| zinc (mg/ml) | 0.108 | 0.108 | 0.108 | 0.108 |

TABLE 12

Survival Curve Analysis

| Test # | insulin sample | median survival (hr) | median survival ratio (X vs. syk-1) | % survival at the end of run |
|---|---|---|---|---|
| Val 21 & 22 (237 hrs) | syk-1 | 36.55 | 1.00 | 0.00 |
| | HRI-A2 | 132.70 | 3.63 | 0.00 |
| | HRI-BJ35 | 210.50 | 5.76 | 16.67 |
| | HRI-TX100 | undefined (>237) | ND (>6.49) | 66.67 |

Figure 8:
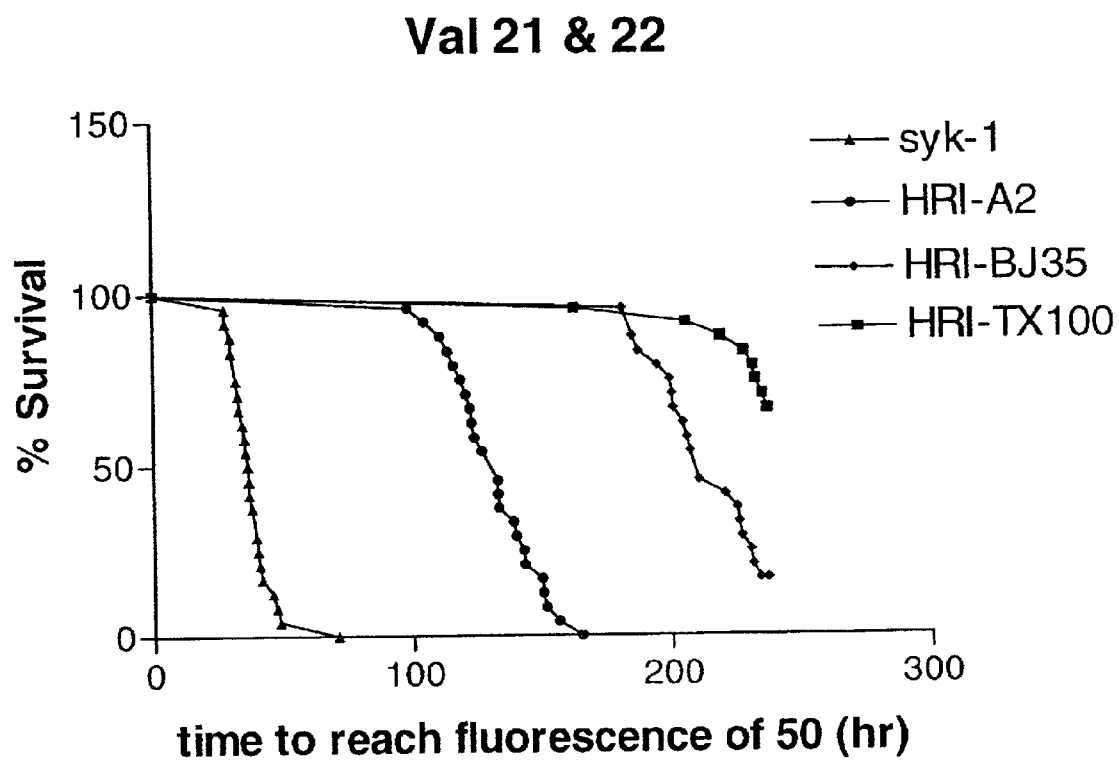
FIG. 8 is a graphic representation of a survival curve comparison of three surfactants for use with insulin formulations of the present invention; the surfactants compared are Genapol PF-10, Brij 35 and Triton X-100.

In this experimental run, these three formulations were compared to the reference batch, syk-1, which included a semi-synthetic insulin and Genapol PF-10, to evaluate the ability of these surfactants to stabilize the tested insulin formulations. The surfactants compared to the Genapol stabilized insulin formulation are Brij 35 and Triton X-100. The results of this experiment are graphically depicted in FIG. 8.

Example 8

Another experiment was performed using HRI-A2, containing Genapol PF-10, as the reference batch. The HRI-A2 formulation was compared to HRI-TW80, containing Tween 80, HRI-BJ-35, containing Brij 35, and HRI-TX-100, containing Triton X-100, in terms of the relative physical stability of these three formulations. Table 12 gives the details of the composition of each tested formulation. Table 13 gives the details of the survival curve analysis for each tested formulation.

TABLE 12

Formulation Summary

| | HRI-A2 | HRI-TW80 | HRI-BJ-35 | HRI-TX-100 |
|---|---|---|---|---|
| insulin type | human recombinant | human recombinant | human recombinant | human recombinant |
| insulin manufacturer | Diosynth | Diosynth | Diosynth | Diosynth |
| insulin concn (units/ml) | 400 | 400 | 400 | 400 |
| Tris (mg/ml) | 6 | 6 | 6 | 6 |
| glycerin (mg/ml) | 17 | 17 | 17 | 17 |
| phenol (mg/ml) | 2.7 | 2.7 | 2.7 | 2.7 |
| surfactant type | Genapol PF10 | Tween 80 | Brij 35 | Triton X-100 |
| surfactant concn (mg/ml) | 0.01 | 0.01 | 0.04 | 0.04 |
| zinc (mg/ml) | 0.108 | 0.108 | 0.108 | 0.108 |

TABLE 13

Survival Curve Analysis

| Test # | insulin sample | median survival (hr) | median survival ratio (X vs. syk-1) | % survival at the end of run |
|---|---|---|---|---|
| Val 23 & 24 (234 hrs) | HRI-A2 | 84.41 | 1.00 | 0.00 |
| | HRI-TW80 | 137.40 | 1.63 | 0.00 |
| | HRI-BJ35 | 182.20 | 2.16 | 12.50 |
| | HRI-TX100 | 186.90 | 2.22 | 8.33 |

Figure 9:
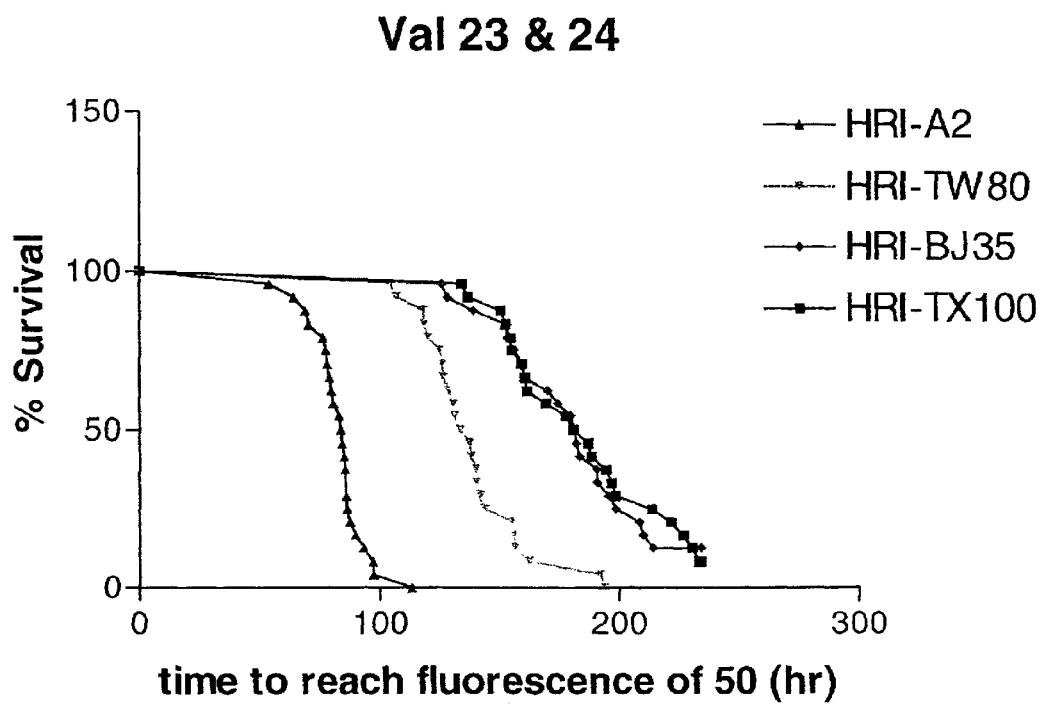
FIG. 9 is a graphic representation of a survival curve comparison of three surfactants for use with insulin formulations of the present invention; the surfactants compared are Tween 80, Brij 35 and Triton-X 100.

In this experimental run, these three formulations were compared to HRI-A2 to evaluate the ability of these surfactants to stabilize the tested insulin formulations. The surfactants compared to the Genapol stabilized insulin formulation are Tween 80, Brij 35 and Triton X-100. The results of this experiment are graphically depicted in FIG. 9.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments and examples are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A method of evaluating the physical stability of a protein formulation, wherein the protein is susceptible to changes in its native conformation that yield non-native conformers of the protein that are preferentially bound by a spectroscopic agent, the method comprising:

(a) preparing a statistically relevant number of identical samples of a protein formulation to yield a first sample type, wherein the protein within the protein formulation is susceptible to changes in its native conformation yielding non-native conformers of the protein;

(b) preparing a statistically relevant number of identical samples of at least one other protein formulation that differs from the first sample type to yield a second, or more, sample types, wherein the protein within at least one other protein formulation is susceptible to a changes in its native conformation yielding non-native conformers of the protein;

wherein the samples prepared in steps (a) and (b) further comprise a spectroscopic agent that exhibits a change in spectra when bound to a non-native conformer of the protein;

(c) applying a controlled stress on all sample types, wherein the controlled stress applied is an interfacial tension or a physical, photochemical or thermal stress which causes the protein to exhibit a change in its native conformation;

(d) monitoring the observable signal produced by the spectroscopic agent in the samples types to yield time-dependent data that are related to a degree of protein conformational change for each sample type;

(e) applying a survival analysis to the data obtained for each sample type; and (f) comparing the survival analysis for each sample type to determine the relative physical stability of the protein formulations under evaluation.

2. The method of claim 1, wherein the controlled stress is agitation comprising shaking at 480–1200 rpm for 3–9 days.

3. The method of claim 1, wherein the protein is insulin and the non-native conformer of the protein is a fibril form of insulin.

4. The method of claim 1, wherein the protein formulation comprises an insulin analogue.

5. The method of claim 1, wherein the spectroscopic agent that exhibits a change in spectra when bound to a non-native conformer of the protein is Thioflavin-T.

6. The method of claim 1, wherein the sample volume of the protein formulations of steps (a) and (b) are from about 1 µl to about 1000 µl.

7. The method of claim 6, wherein the sample volume of the protein of steps (a) and (b) are from about 50 µl to about 500 µl.

* * * * *